United States Patent [19]

Park et al.

[11] Patent Number: 4,474,710

[45] Date of Patent: Oct. 2, 1984

[54] PREPARATION OF HIGHLY BASED MAGNESIUM SULFONATE

[75] Inventors: Chang-Man Park, Naperville, Ill.; Eugene E. Richardson, Kerrville, Tex.

[73] Assignee: Standard Oil Company (Indiana), Chicago, Ill.

[21] Appl. No.: 360,224

[22] Filed: Mar. 22, 1982

[51] Int. Cl.$^3$ .................................... C07C 143/24
[52] U.S. Cl. ........................................ 260/505 N
[58] Field of Search ............................ 260/505 N

[56] References Cited

U.S. PATENT DOCUMENTS 2,467,176 4/1949 Zimmer .................... 260/505 N
2,779,784 1/1957 Sharrah .................... 260/505 N

FOREIGN PATENT DOCUMENTS 958995 5/1964 United Kingdom ........... 260/505 N

Primary Examiner—Alan Siegel
Attorney, Agent, or Firm—Richard A. Kretchmer; William T. McClain; William H. Magidson

[57] ABSTRACT

Instead of total base number of about 30 for an alkaline earth metal sulfonate prepared by reacting up to 200 molar excess of alkaline earth metal compound at a temperature above 104° C. with an alkylbenzene sulfonic acid in the presence of from 0.5 to 10 weight parts of water per 1.0 weight part of alkaline earth metal compound under a pressure of from 2 to 10 atmospheres an oil-soluble magnesium-alkylbenzene sulfonate of total base number of 400 and higher is obtained by reacting at least on 8.5 to 1.0 molar ratios of magnesium oxide to ammonium alkylbenzene sulfonate at a temperature of from 100° C. to 130° C. under autogeneous pressure in the presence of at least 1.1 weight parts of water and 0.3 to 0.5 of methanol per weight part of magnesium oxide. After decompressing and removing water and methanol, the product high base number magnesium alkylbenzene sulfonate is obtained.

2 Claims, No Drawings

PREPARATION OF HIGHLY BASED MAGNESIUM SULFONATE

FIELD OF THE INVENTION

This invention relates to the preparation of an oil soluble, exceptionally high total base number magnesium sulfonate and more particularly pertains to the preparation of such magnesium sulfonate having a total base number of 400 and above. Such magnesium sulfonate has an exceptional reserve basicity making it exceptionally useful as an addition agent for a lubricating oil subjected to rather acidic and corrosive use environments such as a crankcase lubricant for diesel engines which can and do use high sulfur content fuel.

BACKGROUND OF THE INVENTION

One feature of the present invention involves the formation of magnesium hydroxide collodially suspended in a liquid magnesium sulfonate by reaction of magnesium oxide with a liquid hydrocarbon sulfonic acid in the presence of a portion of water relative to magnesium oxide considered by the art to be an appreciable portion of water. For example, one embodiment of the present inventive method involves the use of 11.25 weight parts of water for each 10 weight parts of magnesium oxide and such portion of water relative to alkaline earth metal oxide is indicated in U.S. Pat. No. 2,779,784 (column 2, line 29 and column 3 lines 20 to 23) as an appreciable portion of water relative to the alkaline earth metal oxide.

Said United States Patent is directed to the preparation of basic alkaline earth metal sulfonates containing an amount of alkaline earth metal in excess of the theoretical amount required to neutralize the oil-soluble hydrocarbon sulfonic acid. To accomplish this, said patent teaches that the reaction of the oil soluble sulfonic acid and alkaline earth metal oxide in the presence of the appreciable portion of water must be carried out under superatmospheric pressure (2 to 10 atmosphere at column 3, lines 29–30) to maintain the water in the liquid phase at temperatures above 104.4° C. This combination of pressure and reaction temperature above 104.4° C. is said to be required to form a stable dispersion of the excess alkaline earth metal reactant.

The excess amount of alkaline earth metal reactant related to the stoichiometric requirement to exactly neutralize the sulfonic acid contemplated in U.S. Pat. No. 2,779,784 (column 3, lines 11 to 16) is from 110 up to 220 percent but from a practical standpoint use of an excess of more than 200 percent results in unreacted alkaline earth metal oxide which is removed by an essential filtration step. The alkaline earth metal sulfonate products produced by the elevated temperature and superatmospheric pressure method of said patent conducted for two hours had a total base number of 30.9 and 4.8 which were more than double the total base number of products resulting from the same products not produced under superatmospheric pressure.

We have, however, discovered an improved method for preparing a 400 and higher total base number magnesium sulfonate product in a relatively short reaction time to provide a relatively low viscosity, stable suspension of the excess magnesium reactant.

SUMMARY OF THE INVENTION

A magnesium sulfonate product having a total base number of 400 and higher can be prepared by reacting an ammonium salt of an oil-soluble sulfonic acid at a temperature of from 120° to 130° C. with at least 8.5 gram mole of magnesium oxide per 1.0 gram mole of oil-soluble sulfonic acid in the ammonium salt; in the presence of 1.1 to 1.5 weight parts of water and 0.3 to 0.5 weight part of methanol per 1.0 weight part of magnesium oxide under the autogenous pressure, and then removing methanol and water. The 8.5 mole of MgO per 1.0 mole of oil-soluble sulfonic acid is a 1600% excess over the 0.5 mole of MgO stoichiometrically required to exactly neutralize 1.0 mole of the monobasic sulfonic acid.

The magnesium oxide which does not react with the ammonium sulfonate to form magnesium sulfonate and liberate ammonia in our process, is converted to magnesium hydroxide collodially suspended in the liquid magnesium sulfonate. If desired, the $Mg(OH)_2$ colloidal suspension can be converted by carbonation with $CO_2$ gas to a colloidal suspension of magnesium carbonate.

Following the formation of the colloidal suspension of magnesium hydroxide in the liquid magnesium sulfonate at the reaction temperature of 120° to 130° C., which takes about 15 to 20 minutes, methanol is removed by distillative or evaporative means aided by injection of an inert gas (e.g., nitrogen gas) to strip out methanol to a final temperature of 120°–122° C. The final fluid product after carbonation is clear and bright indicating the presence of little or no filterable solids. Hence the reaction mixture after methanol removal needs no filtration step.

According to a preferred embodiment of our present invention the mixture of magnesium oxide and liquid ammonium salt of a hydrocarbon sulfonic acid are stirred and heated to a temperature of 70° to 75° C. before adding water and methanol thereto. After addition of methanol and water the reaction vessel is closed and its contents are heated to a temperature of from 120° to 130° C. at the autogenetically produced pressure in the closed vessel.

The hydrocarbon sulfonic acid reactant useful in the present inventive method are obtained by the sulfonation of aromatic and alkyl aromatic hydrocarbons which can be fractions of petroleum obtained by its fractionation or extraction. Such sulfonatable hydrocarbons can also be obtained by alkylation of aromatic hydrocarbons, for example, benzene, toluene, the xylenes, cumene, napthalene, alkynaphthalene, diphenyl, alkyldiphenyl, and the like with a chloroalkane or an aliphatic mono-olefin hydrocarbon obtained by dehydrohalogenation of haloparaffins, dehydrogenation of paraffins, dehydration of alcohols, or by polymerization of $C_2$ to $C_4$ mono-olefins and mixture thereof such as the polypropenes, and the polybutenes which are either polymerized isobutane or polymerized mixtures of the butenes. Preferred are the hydrocarbon sulfonic acids obtained by sulfonation of alkylbenzenes derived as petroleum fractions or by alkylation of benzene with a 350 to 800 number average molecular weight viscous liquid polypropene or polybutene. In general the alkyl groups of the petroleum fraction alkylaromatics contain up to 60 carbon atoms while the alkyl groups resulting from alkylation have from 30 up to 65 carbon atoms to make the resulting hydrocarbon (e.g., alkybenzene) sulfonic acids oil-soluble.

The following example will illustrate the practice of the present inventive process.

ILLUSTRATIVE EXAMPLE

The reaction in this illustrative example and the reaction in the comparative example to follow are conducted in a thick wall glass reaction of 400 ml volume suitable for pressurized reactions and equipped with a pressure gauge, thermocouple wall for temperature measurement of the reaction mixture, a magnetic stirrer, a safety pressure-relief valve, a port for charging liquid to or taking a liquid sample from the reacting mixture and adapted to be heated or cooled.

To said reactor there are charged 76.5 grams of a solution in SAE5-W oil of ammonium alkylbenzene sulfonate (0.057 g mole) containing the equivalent of 41% (31.365 grams) of 550 molecular weight hydrocarbon sulfonic acid (alkyl group of 393 average molecular weight) and 20 grams (0.496 gm mole) of magnesium oxide. The resulting mixture is stirred and heated to a temperature of 70° C. Then 25 ml of water and 10.8 ml of methanol are added and the reactor is closed. Thereafter the reactor's contents are stirred and further heated to a temperature of 127° C. (autogenous gauge pressure is 3.5 kg/cm$^2$) and held at a temperature of 124° C. minimum and 127° C. maximum for 15 minutes. The reactor is decompressed and cooled.

The reactor is opened, attached to a product condenser and heated to a final temperature of 121° C. to remove methanol and water.

COMPARATIVE EXAMPLE

The foregoing preparative method is repeated except that after closing the reactor its contents are heated only to a temperature of 77° C. and held at that temperature for 20 minutes before decompressing and removing methanol and water.

The two products prepared by the foregoing examples are carbonated and are compared below.

| Example | MgO Hydration | | Total Base No. | Product | |
|---|---|---|---|---|---|
| | Temp. °C. | Time Min. | | Appearance | Viscosity SSU(2) |
| Illustrative | 124–127 | 15 | 429 | B & C(1) | 501 |
| Comparative | 77 | 20 | 366 | Hazy(3) | 1644 |

(1) B & C is Bright and Clear.
(2) SSU is Saybolt Seconds Universal.
(3) Product is hazy because of large amount of suspended solid material.

The invention claimed is:

1. A method of preparing an oil soluble magnesium alkylbenzene sulfonate having a total base number of 400 and higher which comprises reacting an ammonium alkylbenzene sulfonate whose alkyl-substituent has a molecular weight of from 350 to 800 at a temperature of from 100° C. up to 130° C. with at least 8.5 gram mole of magnesium oxide per 1.0 gram mole of ammonium alkylbenzene sulfonate in the presence of from 1.1 to 1.5 weight parts of water and from 0.3 to 0.5 weight parts of methanol per 1.0 weight part of magnesium oxide in a closed reactor for from 10 to 20 minutes under the autogenetically produced gauge pressure and thereafter decompressing the resulting reaction mixture and removing methanol and water by distillative mean to a final temperature of about 120° C.

2. The method of claim 1 wherein the alkylbenzene sulfonic acid portion of the ammonium sulfonate has a molecular weight of 550.

* * * * *